(12) United States Patent
Niggemann et al.

(10) Patent No.: US 10,982,180 B2
(45) Date of Patent: Apr. 20, 2021

(54) SYSTEM FOR PROPAGATING CELLS

(71) Applicant: INSPHERO AG, Schlieren (CH)

(72) Inventors: Bjoern Niggemann, Schlieren (CH); Jan Lichtenberg, Unterengstringen (CH); Wolfgang Moritz, Bassersdorf (CH); Jens Kelm, Zürich (CH)

(73) Assignee: INSPHERO AG, Schlieren (CH)

( * ) Notice: Subject to any disclaimer, the term of this patent is extended or adjusted under 35 U.S.C. 154(b) by 303 days.

(21) Appl. No.: 15/566,994

(22) PCT Filed: Apr. 15, 2016

(86) PCT No.: PCT/EP2016/058390
§ 371 (c)(1),
(2) Date: Oct. 16, 2017

(87) PCT Pub. No.: WO2016/166315
PCT Pub. Date: Oct. 20, 2016

(65) Prior Publication Data
US 2018/0127698 A1  May 10, 2018

(30) Foreign Application Priority Data
Apr. 16, 2015  (GB) .................................. 1506445.4

(51) Int. Cl.
*C12M 1/32*  (2006.01)
*C12M 1/00*  (2006.01)
(Continued)

(52) U.S. Cl.
CPC ............ *C12M 23/12* (2013.01); *C12M 23/38* (2013.01); *B01L 3/50853* (2013.01); *C12N 5/0018* (2013.01)

(58) Field of Classification Search
CPC ...... C12M 23/12; C12M 23/38; C12M 23/58; B01L 3/50853; B01L 2300/042
See application file for complete search history.

(56) References Cited

U.S. PATENT DOCUMENTS 5,112,574 A   5/1992  Horton
5,282,543 A   2/1994  Picozza
(Continued)

FOREIGN PATENT DOCUMENTS

CN         202482308 U    10/2012
CN    201680035257.8       4/2016
(Continued)

OTHER PUBLICATIONS

International Search Report and Written Opinion dated Jun. 22, 2016 by the International Searching Authority for Patent Application No. PCT/EP2016/058390, which was filed on Apr. 15, 2016 and published as WO 2016/166315 on Oct. 20, 2016 (Inventor—Niggemann et al.; Applicant—Insphero AG) (9 pages).

(Continued)

*Primary Examiner* — William H. Beisner
(74) *Attorney, Agent, or Firm* — Ballard Spahr LLP

(57) ABSTRACT

Provided is a system and a method for propagating cells, the system comprising a multi well plate and a plate sealing means for sealing at least one well of a multiwell plate, the plate sealing means comprising at least one solid bulge or at least one bulge comprising a solid base, said at least one bulge consisting of a resilient elastomer to securely seal at least one well of the multiwell plate. Also disclosed is the use of such a system for propagating cells and the corresponding method.

19 Claims, 7 Drawing Sheets

(51) Int. Cl.
  *B01L 3/00*      (2006.01)
  *C12N 5/00*      (2006.01)

(56)      References Cited

U.S. PATENT DOCUMENTS

| | | | |
|---|---|---|---|
| 2003/0077207 A1* | 4/2003 | Tyndorf | B01L 3/50853 |
| | | | 422/400 |
| 2003/0186217 A1* | 10/2003 | Bader | B01L 3/5025 |
| | | | 435/4 |
| 2003/0235905 A1 | 12/2003 | Spiecker | |
| 2004/0009583 A1 | 1/2004 | Benn | |
| 2010/0196871 A1 | 8/2010 | Dodgson | |
| 2011/0183312 A1 | 7/2011 | Huang | |
| 2011/0263461 A1 | 10/2011 | Kastury | |
| 2014/0322806 A1* | 10/2014 | Bennett | C12M 23/02 |
| | | | 435/325 |

FOREIGN PATENT DOCUMENTS

| | | |
|---|---|---|
| EP | 1122181 A2 | 8/2001 |
| EP | 1864716 A1 | 12/2007 |
| JP | 2010-249520 A | 11/2010 |
| WO | 03/066907 A1 | 8/2003 |
| WO | 2010/105845 A2 | 9/2010 |
| WO | 2011/015864 A1 | 2/2011 |

OTHER PUBLICATIONS

Office Action was dated Jul. 27, 2020 by the Chinese Patent Office for CN Application No. 201680035257.8, filed on Apr. 15, 2016 (Applicant—13318—(Insphero AG.) (English Translation 4 Pages).

* cited by examiner

SYSTEM FOR PROPAGATING CELLS

CROSS-REFERENCE TO RELATED APPLICATIONS

This application claims the benefit of priority under 35 U.S.C. § 371 of International Application No. PCT/EP/2016/058390 filed on Apr. 15, 2016 which claims priority to UK application 1506445.4 filed Apr. 16, 2015. The entire content of these applications is hereby incorporated by reference in their entirety.

FIELD OF THE INVENTION

This invention relates in general to the field of cell cultures. More particularly, the invention concerns a system for propagating living cells, and methods for propagating living cells using said system.

BACKGROUND

For analyzing biological mechanisms and for testing toxicity of drugs or chemical compounds, the use of cells and microtissues becomes increasingly admired. Usually, mammalian cells are cultivated in form of a two dimensional monolayer of cells adhering to a surface of or within the vessel used of cultivating said cell. However, the natural in situ environment of a cell in a living mammalian organism has a three-dimensional architecture. Thus, cultivating mammalian cells in a three-dimensional architecture leading to the formation of spheroids or microtissues provides test systems which more closely resemble the morphological and functional characteristics of a natural environment than a monolayer of cells.

Generating spheroids or microtissues is cumbersome, resource-demanding and fiddly. For this reason, spheroids and microtissues are usually generated in facilities possessing the know-how of propagating 3D cell cultures. For use, the spheroids or microtissues are shipped from where they are generated to the site of their use, for example, in drug screening assays. Typically, cells in culture are cooled down to about 4° C. or are even frozen for being shipped, regardless of whether the cells are present in a two-dimensional or in a three-dimensional architecture. The cooling or freezing of the cells for and during their shipment reduces their metabolism and increases their survival rate. However, at their site of use, the cells have to be thawed and/or warmed up to the temperature at which the subsequent assay is performed. For example, mammalian cells being propagated at 37° C. will be frozen, shipped in liquid nitrogen or dry ice, and warmed up to 37° C. again in such a procedure.

Regardless of how gentle the cooling/freezing and thawing/warming is performed, the viability of the cells within the spheroid/microtissue is affected as the accuracy and/or reliability of the subsequent assay is. Therefore, there is a need for procedures and means which enable propagation and shipping of cells, in particular in form of spheroids or microtissues, without impairing the cell's viability.

Moreover, it is desired to keep the extent of manipulation of spheroids and microtissues during propagation prior to an assay to be performed as well as during the assay as small as possible. Any transfer of spheroids and microtissues from one culture vessel to another culture vessel might affect their integrity and/or functionality. In addition, manipulating cell cultures always renders the cell cultures prone to contamination with unicellular microorganisms such as bacteria or yeasts when the lid of the culture vessel is opened, for example for changing culture media.

Therefore, there is a need for means for culturing cells, in particular in form of microtissues or spheroids, which prevent contamination to the utmost extent.

Mammalian cells may be cultivated in standard SBS/ANSI format multiwell plates which are extensively used in molecular biology laboratories. Multiwell plates are typically rectangular flat plates comprising an array of wells. The precise dimensions (length×width×height) of a multiwall plate of the ANSI (American National Standard Institute) as recommended by the SBS (Society for Biomolecular Screening) are 127.76 mm×85.48 mm×14.35 mm. Multiwell plates come in a variety of formats within said base area but may have a different height. Typical multiwell plates comprise 6 wells in a 2×3 array, each of the wells including a volume of 2 ml to 5 ml;

12 wells in a 3×4 array, each of the wells including a volume of 2 to 4 ml;

24 wells in a 4×6 array, each of the wells including a volume of 0.5 ml to 3 ml;

48 wells in a 6×8 array, each of the wells including a volume of 0.5 to 1.5 ml;

96 wells in a 8×12 array, each of the wells including a volume of 0.1 to 0.3 ml; or 384 wells in a 16×24 array, each of the wells including a volume of 0.03 to 0.1 ml.

The multiwell plates are available in different well formats having either a flat bottom (F-bottom), a flat bottom with minimal rounded edges to the wall (C-bottom), tapered walls (V-bottom) or a bottom in U-shape (U-bottom). Multiwell plates are typically made of polystyrene or polyvinyl chloride. For cell cultures, the surfaces of these products are modified using an oxygen plasma discharge to make their surfaces more hydrophilic so that it becomes easier for adherent cells to grow on the surface which would otherwise be strongly hydrophobic.

Multiwell plates may comprise wells having a circular cross section or wells having a rectangular cross section, preferably a square cross section.

Multiwell plates may be utilized to generate and propagate spheroids or microtissues. For example, multicellular tumor spheroids (MCTS) may be generated in that equal volumes of a suspension of tumor cells is pipetted into agarose-coated wells of a multiwell plate. At the lowest area of the agarose-coating of each well only one spheroid forms, and all spheroids within the multiwell plate will have approximately the same volume. In another approach, microtissues or spheroids may be generated and propagated in hanging drops, wherein specific multiwell plates are used.

During generating and/or propagating spheroids or microtissues in a multiwell plate, for and during storage of multiwell plates containing spheroids or microtissues, as well as for and during shipping multiwell plates containing spheroids or microtissues, the multiwell plates have to be covered. Said covering prevents the cell culture in each well from contamination and secures integrity of the cell culture. Conventional polystyrene lids for multiwell plates are not suitable for shipping multiwell plates containing spheroids or microtissues at ambient temperature, because these conventional lids can not prevent spilling of the well's content. For avoiding any spill, each of the wells of a multiwell plate bearing cells has to be securely sealed.

For sealing multiwell plates that are used in molecular biological methods such as—for example—Polymerase Chain Reaction (PCR) experiments, a number of ways for sealing the plates are known. For example, a foil or plastic film may be applied across the entire upper surface of the plate. Heat sealable aluminum foils provide an efficient gas and liquid tight seal, but they are tiresome to apply and remove.

Certain adhesive plastic films made of polyethylene plates may provide an alternative for sealing multiwell allowing exchange of oxygen, carbon dioxide and water vapor. However, these films are tiresome to apply and to remove. In addition, these films are neither autoclavable nor reusable. Beyond that, the inventors found that sealing multiwell plates bearing spheroids or microtissues with an adhesive polymer film did not prevent substantial loss of viability when the microtissue-bearing multiwell plates were kept at a temperature of between 20° C. and 37° C. compared to conventional lids for multiwell plates.

Surprisingly, the inventors found that loss of viability of the cells of microtissues kept at a temperature of between 20° C. and 37° C. is significantly reduced, if the multiwell plate containing the microtissues is sealed with a specifically configured plate sealing means made of a resilient elastomer. Moreover, said plate sealing means improves handling of microtissue cultures.

SUMMARY OF THE INVENTION

In a first aspect, the invention concerns a system for propagating cells, wherein said system comprises a multiwell plate and a corresponding plate sealing means for sealing at least one well of said multiwell plate.

In a second aspect, the invention concerns a method for propagating microtissues by using the system according to the first aspect.

In a third aspect, the invention concerns the use of the system according to the first aspect for propagating microtissues.

In another aspect, the invention concerns the use of the system in an assay.

In another aspect, the invention concerns a method for investigating the effect of an analyte on living cells.

In a further aspect, the invention concerns the multiwell plate of the system according to the first aspect and its use.

In yet another aspect, the invention concerns the plate sealing means of the system according to the first aspect and its use.

DETAILED DESCRIPTION OF SPECIFIC EMBODIMENTS

Figure 1:
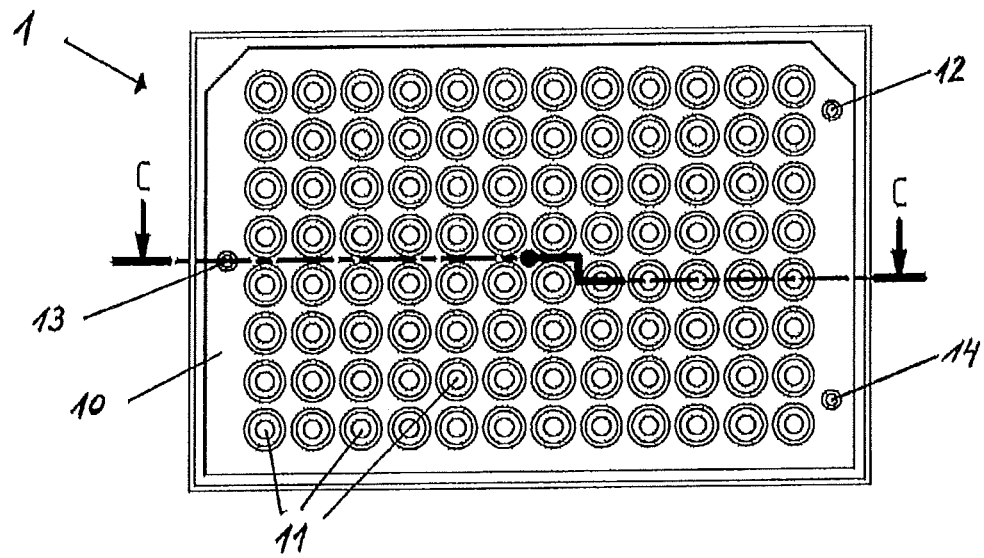
FIG. 1 shows a plane view of an embodiment of the system for propagating cells.

The present invention will be described with respect to particular embodiments and with reference to certain drawings but the invention is not limited thereto but only by the claims. The drawings described are only schematic and are non-limiting. In the drawings, the size of some of the elements may be exaggerated and not drawn on scale for illustrative purposes. The dimensions and the relative dimensions do not correspond to actual reductions to practice of the invention.

Furthermore, the terms first, second and the like in the description and in the claims, are used for distinguishing between similar elements and not necessarily for describing a sequence, either temporally, spatially, in ranking or in any other manner. It is to be understood that the terms so used are interchangeable under appropriate circumstances and that the embodiments of the invention described herein are capable of operation in other sequences than described or illustrated herein.

It is to be noticed that the term "comprising", used in the claims, should not be interpreted as being restricted to the means listed thereafter; it does not exclude other elements or steps. It is thus to be interpreted as specifying the presence of the stated features, integers, steps or components as referred to, but does not preclude the presence or addition of one or more other features, integers, steps or components, or groups thereof. Thus, the scope of the expression "a device comprising means A and B" should not be limited to devices consisting only of components A and B. It means that with respect to the present invention, the only relevant components of the device are A and B.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments.

Similarly it should be appreciated that in the description of exemplary embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the detailed description are hereby expressly incorporated into this detailed description, with each claim standing on its own as a separate embodiment of this invention.

Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

Furthermore, some of the embodiments are described herein as a method or combination of elements of a method that can be implemented by a processor of a computer system or by other means of carrying out the function. Thus, a processor with the necessary instructions for carrying out such a method or element of a method forms a means for carrying out the method or element of a method. Furthermore, an element described herein of an apparatus embodiment is an example of a means for carrying out the function performed by the element for the purpose of carrying out the invention.

In the description provided herein, numerous specific details are set forth. However, it is understood that embodiments of the invention may be practiced without these specific details. In other instances, well-known methods, structures and techniques have not been shown in detail in order not to obscure an understanding of this description.

The invention will now be described by a detailed description of several embodiments of the invention. It is clear that other embodiments of the invention can be configured according to the knowledge of persons skilled in the art without departing from the true spirit or technical teaching of the invention, the invention being limited only by the terms of the appended claims.

According to the first aspect, the invention provides a system for propagating cells, wherein the system comprises a multiwell plate and a plate sealing means for sealing at least one well of the multiwell plate, such that cells within the at least one well of the multiwell plate can be propagated therein when the plate sealing means is applied to the multiwell plate.

The term "cells" as used herein refers to one or more living cells, either prokaryotic cells or eukaryotic cells. The eukaryotic cells may be of fungal, plant or animal origin. The term "cells" includes human cells, i.e. cells of human origin. The term "cells" comprises cells being present in form of individual cells, in form of a monolayer of cells and also cells in form of a spheroid or microtissue.

The term "microtissue" refers to an assembly of cells attached to one another. Said assembly of cells may either be present in form of a monolayer of cells or in form of a three dimensional structure. Hence, the term "microtissue" as used herein also comprises spheroids.

The term "propagating" with respect to cells and/or microtissues refers to all aspects of cultivating cells. The term "propagating" as used herein comprises the cultivation of cells including their multiplication, development, proliferation and maturation. Thus, "propagating" also comprises the formation of microtissues. The term "propagating" as used herein also comprises the maintenance, storage and/or shipping of cells and/or microtissues in culture.

In an embodiment, the multiwell plate of the system is a typical standard SBS/ANSI format multiwell plate, preferably a multiwell plate as described herein above, more preferably a multiwell plate comprising 96 wells in a 8×12 array or 384 wells in a 16×24 array.

In an additional and/or alternative embodiment, at least a portion of at least one well of the multiwell plate, preferably at least a portion of all wells of the multiwell plate, is/are provided with an ultra-low attachment surface. Propagating cells in a well which is provided with an ultra-low attachment surface maintains the cells in a suspended, unattached state. Propagating a spheroid or microtissue in a well that is provided with an ultra-low attachment surface maintains integrity of the spheroid or microtissue, and prevents the spheroid or microtissue from undesired attachment-mediated maturation or differentiation, including an undesired alteration in cell division properties.

Providing a well of a multiwell plate with an ultra-low attachment surface can be done in various different ways. An example of providing a well with an ultra-low attachment surface is covalently binding a hydrogel layer to the substrate such as polystyrene, said hydrogel being hydrophilic and neutrally charged. Multiwell plates comprising such an ultra-low attachment surface are commercially available from Corning Inc. Another example of an ultra-low attachment surface is a surface made of a polymer consisting of 2-methacryloyloxyethyl phosphorylcholine (MPC). Such surfaces are available from NOF America Corporation under the tradename Lipidure®.

Thus in an additional and/or alternative embodiment, at least a portion of at least one well of the multiwell plate, preferably at least a portion of all wells of the multiwell plate comprises a coating layer consisting of a hydrogel such as agarose, or a coating layer consisting of 2-methacryloyloxyethyl phosphorylcholine (MPC).

In an additional and/or alternative embodiment, at least two neighboring wells of the multiwell plate are in fluid communication. In a preferred embodiment, the wells of a row of wells within the multiwell plate are in fluid communication with each other. For example, in a 96 well multiwell plate the 12 wells of up to 8 rows of wells or 8 wells of up to 12 rows of wells can be in fluid communication. In an alternative embodiment, all wells of a multiwell plate are in fluid communication with each other. Preferably, the wells of a row of wells or the wells of the multiwell plate are in fluid communication with each other in that each neighboring wells are in fluid communication.

In a preferred embodiment, the fluid communication between at least two wells of the multiwell plate is established in that at least one channel is provided between said at least two wells.

Preferably, the fluid communication between the two or more wells of the multiwell plate is established by means of at least one channel that is provided between two wells being in direct fluid communication with each other. In alternative embodiments, one, two, three, four or even more channels can be provided between the two wells being in direct fluid communication with each other. In embodiments comprising two or more channels between two wells being in direct fluid communication with each other, said channels run in parallel.

The diameter of the at least one channel and/or the number of channels between two wells can be chosen to control the flow rate of the fluid from one well to the other well. Generally, the lower the number of channels and the smaller its/their diameter, the smaller the flow rate of the medium that may migrate from one well to the next well.

Providing a fluid communication between at least two wells of the multiwell plate permits the system's use for assays wherein the effect of a metabolite of product produced by the cells in one well on the cells with the other well can be determined without any need of opening the sealing of the wells and can also avoid the need of aspirating culture medium from wells bearing cells.

The plate sealing means comprises at least one bulge consisting of a resilient elastomer, wherein the bulge is configured to securely fit into a well of the multiwell plate. The term "resilient" means that the material is able to return to its original shape after being pulled, stretched, pressed or bent without permanent deformation or rupture. Thus, the bulge fits into the opening of the well, and due to its resilience securely seals the well. The term "securely sealing" means that the bulge does not drop out of the well when the system is turned upside down, and that no fluid inside the well leaks out of the sealed well when the system is turned upside down.

In an additional and/or alternative embodiment, the at least one bulge is a solid bulge. The at least one bulge may be configured as a frustrum of a cone or as a frustrum of an inverse cone. In an additional and/or alternative configuration, the at least one bulge comprises a concave bottom for providing an obstruse angle between the wall of the well and the bulge when the bulge is appropriately inserted into said well. The term "bottom" with respect to a bulge refers to the distal end of the bulge, i.e. the end of the bulge being opposite of its base. In an additional and/or alternative configuration, the at least one bulge comprises a hollowed out bulge for improved flexibility and fit of said at least one bulge into a corresponding well. The hollowing out of the bulge provides a flexible edging of the bulge which improves fit of the at least one bulge in the well and sealing of the well. In yet an additional and/or alternative embodiment, the at least one bulge comprises at least one flap. Preferably, the at least one bulge comprises a single flap or a double flap. Said at least one flap is circumferentially arranged at the outer edge of the distal portion of the at least one bulge. The distal portion of the at least one bulge is understood to be the portion opposite of the bulge's base. Notwithstanding, the configurations comprising a concave bottom, a hollow out and/or at least one flap comprise a base portion being solid in its entire cross section.

In an additional and/or alternative embodiment, the resilient elastomer is a silicone rubber.

A preferred silicone rubber has a hardness of Shore A in the range of 55 to 65, measured according to DIN 53505.

A preferred silicone rubber has a specific gravity of between about 1.13 and 1.17 g/cm3, measured according to DIN 53479.

A preferred silicone rubber has a tensile strength of about 7 MPa, measured according to DIN 53504 S2.

A preferred silicone rubber has an elongation of about 350%, measured according to DIN 53504 S2.

In an additional and/or alternative embodiment, the resilient elastomer is selected from the group consisting of silicone rubber, preferably dimethylsilicone rubber vinyl methyl siloxane, and phenyl vinyl methyl siloxane, fluorosilicone rubber, and nitrile rubber and natural rubber.

In an additional and/or alternative embodiment, the resilient elastomer is gas permeable. This is, that gas such as—for example—air, oxygen and carbon dioxide—can permeate through the silicone rubber. In an additional and/or alternative embodiment, of the gas permeable resilient elastomer has an oxygen permeability of more than $1*10^9$, $cm^3*cm/(s*cm^2*cmHg)$.

In an additional and/or alternative embodiment, the plate sealing means is antistatic. This is, the silicone rubber material of the plate sealing means reduces or even eliminates static electricity.

In an additional and/or alternative embodiment, the plate sealing means is autoclavable. That is, the plate sealing means can be sterilized without being damaged or impaired in its functionality as described herein by subjecting them to high pressure saturated steam at 121° C. for around 15 to 20 minutes.

In an additional and/or alternative embodiment, the plate sealing means is reuseable. This is, the plate sealing means can be used multiple times for sealing a multiwell plate without being damaged or impaired in its functionality.

In an additional and/or alternative embodiment, the plate sealing means comprises at least one bulge comprising a resealable septum. This is, the plate sealing means may be punctured by means of a 18 gauge needle and reseals when the 18 gauge needle is pulled out of the plate sealing means.

The properties such as gas-permeability is not significantly altered upon puncturing.

In an additional and/or alternative embodiment, the plate sealing means is non-adhesive. This is, the plate sealing means does not have a tack.

In an additional and/or alternative embodiment, the at least one bulge of the plate sealing means comprises a rim at its base, i.e. where the bulge protrudes from the second face. The rim of the at least one bulge is circumferential. The rim of the at least one bulge is configured not to fit into a well of a corresponding multiwell plate, but to sit on top of the well next to the well's aperture.

The rim prevents the second face of the plate sealing means from getting into contact with the upper face of the multiwell plate. This configuration permits easier removal of the plate sealing means from the multiwell plate compared to an embodiment without such rims.

The at least one bulge may have a circular cross section, a rectangular cross section of a square cross section. The sides of the bulge are configured to narrow the cross section from the base of the bulge towards the tip of the bulge. In an embodiment, the opposite sides of a bulge include an angle of 30° which corresponds to an angle of 15° between the longitudinal axis of the bulge and the flange.

An angle of approximately 30° between the sides of a bulge permits easy insertion and removal of the bulge into/from a well of a corresponding multiwell plate, but secures tight and snugly fitting of the know within the well.

In an additional and/or alternative embodiment, the plate sealing means is present in form of a resilient mat made of a gas-permeable, antistatic silicone rubber. The plate sealing means of this embodiment comprises a first face and a second face. The first face constitutes the upper face of the plate sealing means when the plate sealing means is in use, i.e. applied to a multiwell plate. Thus, the first face of the plate sealing means faces away from the multiwell plate when the plate sealing means is applied to a multiwell plate. The second face of the plate sealing means is at the opposite side of the first face of the plate sealing means and constitutes the lower face, i.e. the face of the plate sealing means facing the multiwell plate when the plate sealing means is in use, i.e. applied to a multiwell plate.

In an embodiment, the first face has a flat or even surface substantially free from dimples. In an additional and/or alternative embodiment, the first face has labelling means for better identifying those areas of the first face being aligned with the wells of a multiwell plate when the plate sealing means is applied to a multiwell plate. The labelling means may be an embossed, imprinted or engraved structure. The labelling means may comprise letters, numbers or combinations of letters and numbers unique for each well, rims or walls indicating the position of each well, wherein the labelling means are arranged on the first face of the plate sealing means at positions corresponding to the wells of the multiwell plate, i.e. opposite of bulges protruding from the second face of the plate sealing means.

The plate sealing means in form of the resilient mat comprises at least one bulge protruding from the second face of the plate sealing means. Preferably the plate sealing means comprises an array of bulges protruding from the second face of the plate sealing means, wherein the array of bulges matches the array of wells of a corresponding multiwell plate, i.e. of a multiwell plate said plate sealing means is configured to seal. The at least one bulge, preferably each bulge of the array of bulges, is/are sized and shaped to sit firmly in a well of the corresponding multiwell plate.

The at least one bulge or the bulges or the array of bulges are solid elements of the plate sealing means protruding from the second face of the plate sealing means or elements comprising a solid base portion. That is, the bulges are solid or comprise a solid base, and they consist of the silicone rubber, the plate sealing means are made of such that the at least one bulge or the bulges are integral elements of the plate sealing means such that the thickness of the rubber material is increased in the area of the bulges compared to the area between two bulges. The bulges are not configured as dimples which are typically generated in that the rubber film is deformed such that the thickness of the rubber material in the area of the dimple is essentially the same as outside of the dimple.

The bulges provide a secure sealing of the wells of a corresponding multiwell plate when the plate sealing means is applied to the multiwell plate, thus preventing any liquids from escaping from or entering the well that is sealed. It is believed that the tight sealing of the wells is based on the fact that the bulge is solid or comprises a solid base rather than being a dimple. The restoring force of the resilient bulge when inserted into the well of the multiwell plate appears to be higher than the restoring force of a dimple having the same shape and size. Therefore, it is believed that the better sealing of a bulge compared to a dimple accounts for the improvement in cell viability.

Additional configurations of the bulge further improve their efficacy in sealing a well and thereby securing propagation of cells within the well. Such additional configurations are—for example—a concave bottom of the bilge, a hollow out of the bulge and/or at least one circumferential flap at the distal portion of the bulge.

The plate sealing means comprising solid bulges or bulges comprising a solid base is made of a resilient elastomer. Thus, a flexible mat is provided that can be easily applied to a multiwell plate, easily removed from the multiwell plate and easily re-applied to the same or another multiwell plate, and simultaneously provide a tight sealing of the wells of a multiwell plate.

In an embodiment, the plate sealing means covers the entire surface of the multiwell plate. In an alternative embodiment, the plate sealing means does not cover the entire surface of the multiwell plate, but only a portion of the surface.

The plate sealing means comprises a resilient silicone mat which covers essentially the entire upper surface of a standard 96-well plate, and comprises 96 bulges such that every well of a standard 96 well plate can be sealed using this embodiment of the plate sealing means.

In an embodiment, the plate sealing means comprises a circumferential brim. The brim extends perpendicular to the plane of the mat and in the direction of the bulges. Thus when mounted to a multiwell plate the brim of the plate sealing means encompasses the sides of the multiwell plate. Thus the embodiment of the plate sealing means has the form a conventional polystyrene lid for multiwell plates, but is resilient.

The bulges preferably have a circular cross section for securely fitting into wells having a circular cross section too. It is understood that the bulges of the plate sealing means may be configured as described herein before with respect to the bulges.

The term "multiwell plate" as used herein refers to rectangular flat plates to comprising an array of wells, preferably having dimensions as recommended by the Society for Biomolecular Screening as set forth herein above.

The term "corresponding multiwell plate" as used herein refers to a multiwell plate which has the same number of wells as the plate sealing means has bulge, wherein the wells of the multiwall plate are present in the same array as the bulges of the plate sealing means are, and/or wherein the wells have the same cross section as the bulges of the plate sealing means have, and where the diameter of the well is identical to the diameter of the bulge at about half of its height. The term "corresponding multiwell plate" shall indicate that the plate sealing means is a plate sealing means configured for sealing the wells of a specific multiwell plate.

The term "cultivating" as used herein comprises maintaining or propagating cells in vitro, wherein the term "maintaining" comprises storage of cells at lower temperatures, for example at about 4° C., or even frozen, for example at about −20° C., about −80° C. or even at about −180° C. The term "cultivating" comprises proliferation of cells in vitro as well as the maintenance of cells in vitro, i.e. under conditions where the cells multiply, multiply at a reduced speed, or do not multiply.

The term "shipping" as used herein refers to freight transport, i.e. the physical process of transporting commodities and merchandise goods and cargo including living organs, tissues, microtissues, spheroids and cells. The term "shipping" comprises transport by sea, by land or air.

In an embodiment the plate sealing means is made of a resilient elastomer, the resilient elastomer is preferably selected from the group consisting of silicone rubber, preferably dimethylsilicone rubber vinyl methyl siloxane, and phenyl vinyl methyl siloxane, fluorosilicone rubber, and nitrile rubber and natural rubber.

In an embodiment, the resilient elastomer of the plate sealing means is gas permeable. This is, that gas such as—for example—air, oxygen and carbon dioxide—can permeate through the elastomer. Preferably, the resilient elastomer has an oxygen permeability of more than $1*10^9$, $cm^3*cm/(s*cm^2*cm\ Hg)$.

A preferred silicone rubber has a hardness of Shore A in the range of 55 to 65, measured according to DIN 53505.

A preferred silicone rubber has a specific gravity of between about 1.13 and 1.17 g/cm3, measured according to DIN 53479.

A preferred silicone rubber has a tensile strength of about 7 MPa, measured according to DIN 53504 S2.

A preferred silicone rubber has an elongation of about 350%, measured according to DIN 53504 S2.

The plate sealing means is antistatic. This is, the silicone rubber material of the plate sealing means reduces or even eliminates static electricity.

The plate sealing means is autoclavable. That is, the plate sealing means can be sterilized without being damaged or impaired in its functionality as described herein by subjecting them to high pressure saturated steam at 121° C. for around 15 to 20 minutes.

The plate sealing means is reuseable. This is, the plate sealing means can be used multiple times for sealing a multiwell plate without being damaged or impaired in its functionality.

In an additional embodiment, the plate sealing means comprises at least one bulge comprising a resealable septum. This is, the plate sealing means may to be punctured by means of a 18 gauge needle and reseals when the 18 gauge needle is pulled out of the plate sealing means. The properties such as gas-permeability is not significantly altered upon puncturing.

The plate sealing means is non-adhesive. This is, the plate sealing means does not have a tack.

In an additional embodiment, the at least one bulge of the plate sealing means comprises a rim at its base, i.e. where the bulge protrudes from the second face. The rim of the at least one bulge is circumferential. The rim of the at least one bulge is configured not to fit into a well of a corresponding multiwell plate, but to sit on top of the well next to the well's aperture.

The rim prevents the second face of the plate sealing means from getting into contact with the upper face of the multiwell plate. This configuration permits easier removal of the plate sealing means from the multiwell plate compared to an embodiment without such rims.

The at least one bulge may have a circular cross section, a rectangular cross section of a square cross section. The sides of the bulge are configured to narrow the cross section from the base of the bulge towards the tip of the bulge. In an embodiment, the opposite sides of a bulge include an angle of 30° which corresponds to an angle of 15° between the longitudinal axis of the bulge and the flange.

An angle of approximately 30° between the sides of a bulge permits easy insertion and removal of the bulge into/from a well of a corresponding multiwell plate, but secures tight and snugly fitting of the know within the well.

In an embodiment, the plate sealing means comprises a circumferential brim. The brim extends perpendicular to the plane of the mat and in the direction of to the bulges. Thus when mounted to a multiwell plate the brim of the plate sealing means encompasses the sides of the multiwell plate. Thus the embodiment of the plate sealing means has the form a conventional polystyrene lid for multiwell plates, but is resilient.

The plate sealing means may additionally comprise posts or pins fitting respectively into holes other than the wells within a multiwell plate. The posts are shaped such that they fit into the holes and contact the walls of the holes. The posts/holes are further means preventing the plate sealing means from moving laterally with respect to the multiwell plate, and prevent misalignment of the plate sealing means, in particular when the plate sealing means is only partially removed from the multiwell plate, for instance when access to individual wells of the multiwell plate is required.

In an embodiment, the plate sealing means comprise at least one inlet opening and at least one outlet opening. In a preferred embodiment, the plate sealing means comprises an inlet opening and an outlet opening for each row of wells within the multiwell plate. Preferably, each of the inlet openings of the plate sealing means corresponds to the first well of the row of wells, whereas the outlet well corresponds to the last well of the row of wells. Said at least one inlet opening and said at least one outlet opening are holes or through bores in the plate sealing means such that the corresponding well of the multiwell plate is not sealed by the plate sealing means when the plate sealing means is mounted to the multiwell plate.

The inlet opening permits adding or supplementing culture medium to the at least one well. The outlet opening permits removal or aspiration of culture medium from the at least one well. In combination with the embodiment of the multiwell plate comprising at least two wells being in fluid connection, mounting of the plate sealing means comprising at least one inlet opening and one outlet opening permits supplementing all wells with culture medium that are in direct or indirect fluid connection with inlet well.

In a further embodiment, the at least one inlet opening and/or the at least one outlet opening of the plate sealing means are configured as funnel or chimney. "Funnel" refers to a structure having a diameter narrowing towards the point of connection to the plane of the silicone mat, at least along of at least a portion of its longitudinal direction. "Chimney" refers to a pipe or tube like structure having a constant diameter along its longitudinal direction.

In another embodiment, the plate sealing means is configured in in form of a substantially planar resilient mat without bulges. In this embodiment, the plate sealing means comprises a rigid frame, preferably made of hard plastics such as polystyrene, and is configured to be used as a lid for a corresponding multiwell plate. Said rigid frame comprises a plate comprising bores, wherein said bores align to the wells of a corresponding multiwell plate. Said plate comprises an outer face and an inner face. The outer face faces away from the multiwell plate, whereas the inner face faces towards the multiwell plate upon mounting the plate sealing means to the multiwell plate. The substantially planar resilient mat is provided on the inner face of the plate.

In an additional and/or alternative embodiment, the system comprises a quick lock system for securing the rigid frame to the multiwell plate. In an embodiment, the quick lock system comprises at least two locking latches at opposite ends of the frame. Said latches engage with grooves or slots or trenches at the corresponding positions at the outer circumference of the corresponding multiwell plate. By forcing the frame onto the multiwell plate, the latches engage and thereby not only secures the frame onto the multiwell plate, but simultaneously sealing the wells of the multiwell plate.

In a preferred embodiment of the multiwell plate for being sealed by the plate sealing means of the latter embodiment, each well comprises a circumferential edge at its outlet opening. Said circumferential edge protruding from the upper face of the multiwell plate in perpendicular direction thereto. Said circumferential rim is pressed into the planar resilient mat when the plate sealing means is mounted to the multiwell plate, thereby providing the secure sealing if the well.

The substantially planar resilient mat is made of a resilient elastomer as described herein before with respect to the bulges.

Figure 2:
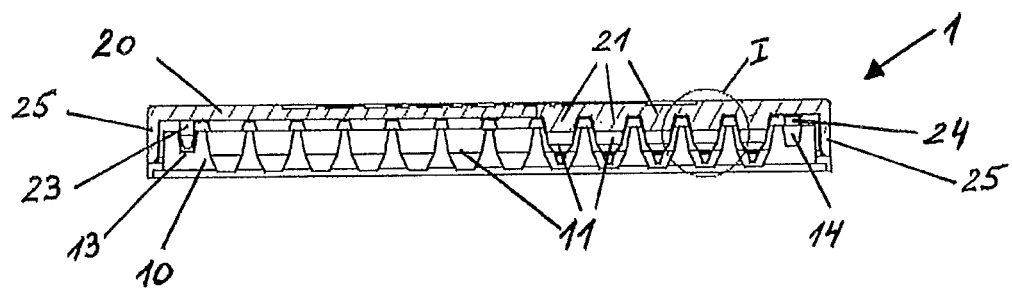
FIG. 2 shows a cross-sectional view along line C-C of the embodiment shown in FIG. 1.
Figure 3:
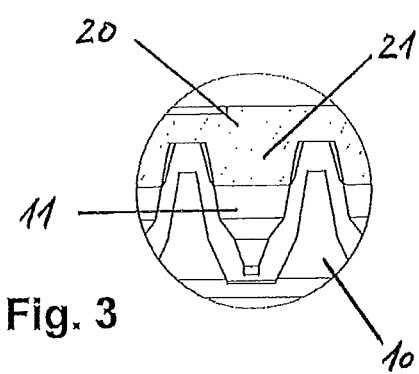
FIG. 3 shows an enlarged view of the encircled section within the cross-sectional view of the embodiment shown in FIG. 2.

Referring to FIGS. 1 to 3 an embodiment of the system (1) for propagating microtissues is displayed. FIG. 1 shows a perspective view on top of the system (1). The embodiment comprises a 96-well multiwell plate (10) comprises a plurality of wells (11) being arranged in a 12×8 array. The multiwell plate (10) is covered with an embodiment of a plate sealing means (20, not shown in FIG. 1).

The embodiment of the multiwell plate (10) comprises three positioning means (12, 13, 14) in form of apertures. The three positioning means (12, 13, 14) are arranged such that a lid or a plate sealing means (20) comprising corresponding protuberances (22, 23, 24) which are configured for engaging said positioning means (12, 13, 14) can be applied to the multiwell plate (10) in one specific orientation only.

The plate sealing means (20) comprises a plurality of bulges (21) protruding from one face of the plate sealing means. The plurality on bulges (21) are present in the same array as the wells of the corresponding multiwell plate. In the embodiment shown in FIGS. 1 to 3, the plurality of bulges (21) are arranged in a 12×8 array.

The presence of the positioning means (12, 13, 14) prevents a plate sealing means (20) comprising a symmetrical array of bulges (21) to the applied to the multiwell plate (10) in an inadvertent orientation. Thereby avoiding contamination.

In addition, the embodiment of the plate sealing means (20) shown in FIG. 2 comprises a circumferential brim (25) at the outer border of the plate sealing means (20). The brim (25) extends the sides of the plate sealing means (20) over the upper surface of the multiwell plate (10) when the plate sealing means (20) is appropriately mounted to the multiwell plate (10).

FIG. 3 illustrates how a bulge (21) of the plate sealing means (20) snugly fits into the corresponding well (11) of a corresponding multiwell plate (10) providing a tight seal of the well (11) due to its size and resilience. The bulge (21) is configured to leave a volume for cells, culture medium and/or air in the well (11).

Figure 4:
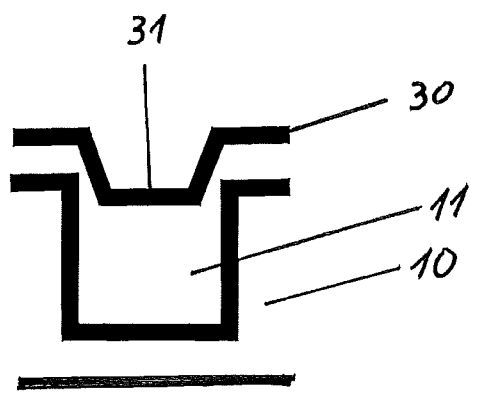
FIG. 4 shows a partial cross-sectional view of a plate sealing means according to prior art and a well of a corresponding multiwell plate.

FIG. 4 shows a cross-sectional view of a part of a commercially available plate sealing means (30). The view represent a single well of the multiwell plate and the corresponding section of a commercially available plate sealing means (30). The commercially available plate sealing means (30) consists of a film that has been subjected to an embossing process such that dimples (31) are generated. Said dimples (31) are configured to fit into a well (11) of a corresponding multiwell plate (10). The thickness of the film in the areas of the dimples is the same as in the areas next to the dimples.

Figure 5:
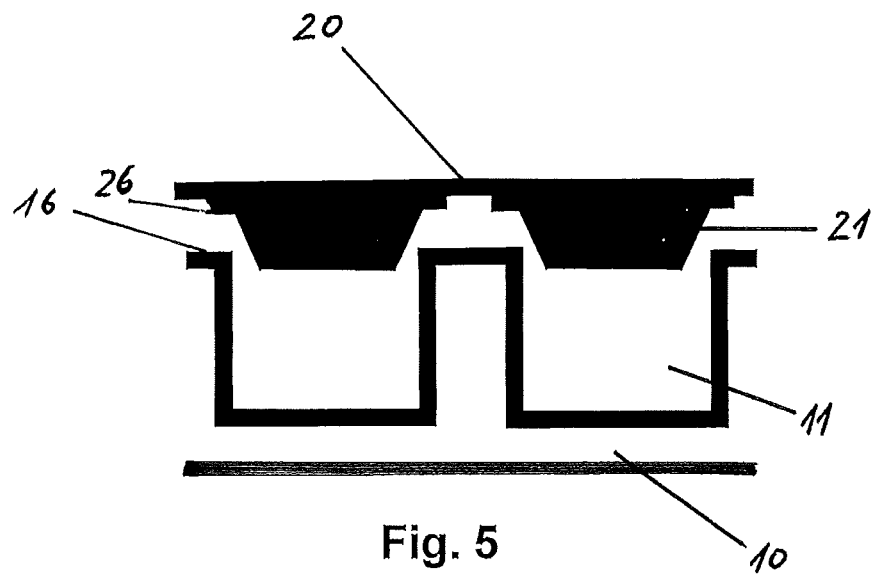
FIG. 5 shows a partial cross-sectional view of an embodiment of the plate sealing means of the invention and two adjacent wells of a corresponding multiwell plate.

Referring to FIG. 5 showing a cross-sectional view of a part of an embodiment of a system according to the invention. The part represents two neighboring wells (11) of a multiwell plate (10), and the corresponding section of a corresponding plate sealing means (20). The figure illustrates that the plate sealing means (20 comprises bulges (21) which are solid elements of the plate sealing means (20) were the material of the plate sealing means (20) is much thicker than in the region between the bulges (21).

The bulges (21) of the embodiment of the plate sealing means (20) as shown in FIG. 5 comprise a rim (26) at the base of the bulges (21), i.e. where the bulges (21) protrude from the plane of the plate sealing means (20). Upon sealing of a well (11) of a corresponding multiwell plate (10), the bulges (21) fit snugly into the open end of the well (11) such that the rim (26) resides on the upper face (16) of the multiwell plate (10). The rim (26) of each bulge (21) is a circumferential element. The presence of said rims (26) at each bulge (21) renders removal of the plate sealing means (20) from the corresponding multiwell plate (10) after the plate sealing means (20) being mounted to the multiwell plate (10) much easier, thereby preventing undesired shaking which might affect formation and/or integrity of a microtissue within a well of the multiwell plate (10) and/or might lead to undesired spillover of culture medium from one well to the other.

Figure 6:
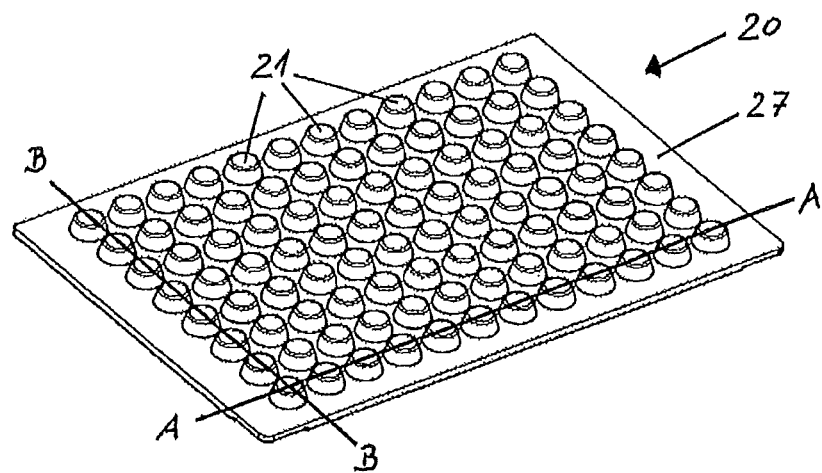
FIG. 6 shows a perspective view of an embodiment of a plate sealing means of an embodiment of the system for propagating cells.

Referring to FIGS. 6 to 9 an embodiment of the plate sealing means (20) is displayed. FIG. 6 shows a perspective view on top of the second face (27) of the plate sealing means (20). The embodiment of the plate sealing means (20) as shown comprises an array of solid bulges (21) protruding from the second face (27). The plurality of solid bulges (21) are arranged in an 8×12 array corresponding to the array of wells of a typical 96-well plate.

Figure 7:
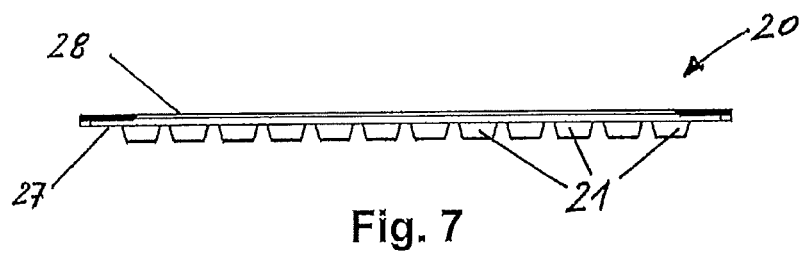
FIG. 7 shows a cross-sectional view along line A-A of the embodiment shown in FIG. 6.
Figure 8:
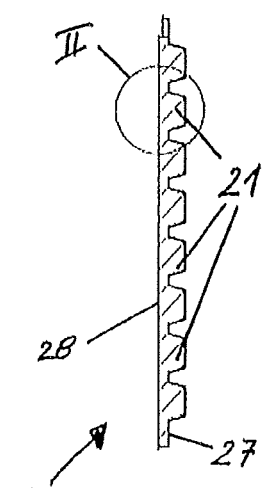
FIG. 8 shows a cross-sectional view along line B-B of the embodiment shown in FIG. 6.

FIG. 7 illustrates a longitudinal section along line A-A of the plate sealing means (20) of FIG. 6, whereas FIG. 8 illustrates a longitudinal section along line B-B of the plate sealing means (20) of FIG. 6.

Figure 9:
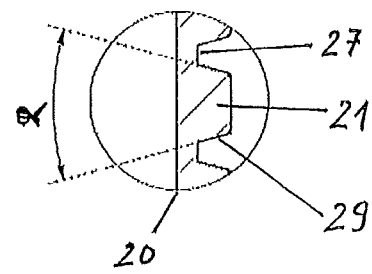
FIG. 9 shows an enlarged view of the encircled section within the cross-sectional view of the embodiment shown in FIG. 8.

FIG. 9 is an enlarged view of portion II encircled in FIG. 8. FIG. 9 emphasis a solid bulge (21) of the plate sealing means (20) which protrudes from the second face (27) of the plate sealing means.

The solid bulges (21) protruding from the second face (27) of the plate sealing means (20) preferably have a height of about 1.5 times the thickness of the mat, i.e. the distance measured from the first face (28) to the second face (27) of the mat. The bulges (21) comprise a base where they merge with the second face (27) of the plate sealing means (20), and a tip. The sides (29) of each bulge (21) are tapered such that the diameter of the bulge (21) is at its tip is smaller than the diameter at the base of the bulge (21). The flanges (29) on opposite sides of the solid bulge (21) include an angle ($\alpha$) of about 30° such that the bulge can be easily inserted into a well of a corresponding multiwell plate, fits snuggly into the well, and provides a tight seal of the well. The sides are preferably tapered in that they include an angle (7) of about 30°.

Figure 10:
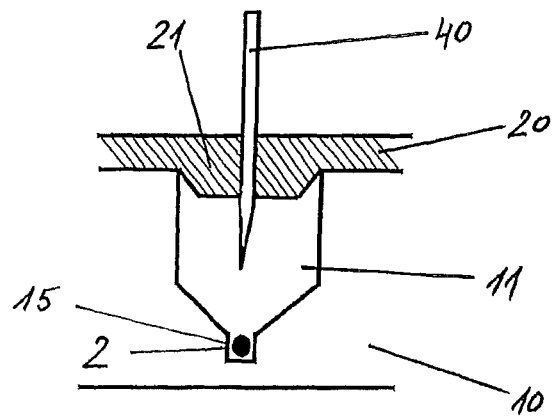
FIG. 10 shows a cross section through a portion of an embodiment of the system.

FIG. 10 illustrates a portion of a further embodiment of a system, wherein the plate sealing means (20) comprises at least one solid bulge (21) for sealing the corresponding well (11) of a corresponding multiwell plate (10). The bulge (21) comprises a self-sealing septum such that, for example, an injection needle (40) can be poked through the self-sealing septum of the bulge (21). Using a syringe or other suitable means, culture medium can be aspirated trough the injection needle (40) from the well (11) and/or added thereto without the need of removing the entire plate sealing means (20) from the multiwell plate (10). Upon removal of the injection needle (40), the septum seals itself such that the plate sealing means (20) still provides a tight seal of the well (11).

Also shown in FIG. 10 is an embodiment comprising a specifically designed well (11) for propagating microtissues (2). Said well (11) comprises a microtissue culture compartment (15) which is present at the bottom of the well (11). Said microtissue culture compartment (15) is a small partition in the middle of the bottom of the well which is in fluid connection therewith and thus constitutes an integral part of the well.

Figure 11:
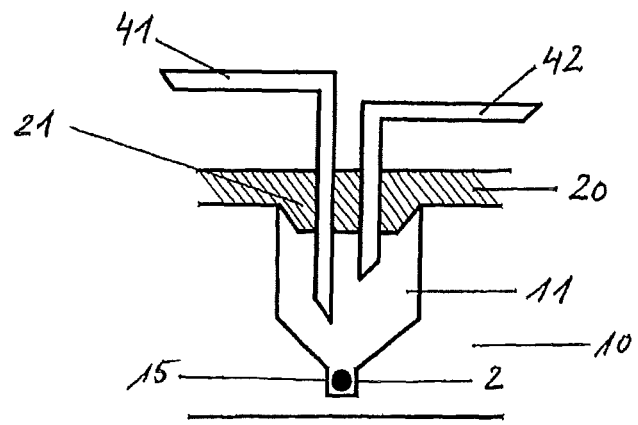
FIG. 11 shows a cross section through a portion of another embodiment of the system.

FIG. 11 illustrates a portion of another embodiment, wherein the plate sealing means (20) comprising a bulge (21) with two self-sealing septa. This embodiment permits inserting an inlet conduit (41) and an outlet conduit (42) through the plate sealing means (20) into the well (11). This configuration permits providing a constant flow of culture medium through the well (11).

Figure 12:
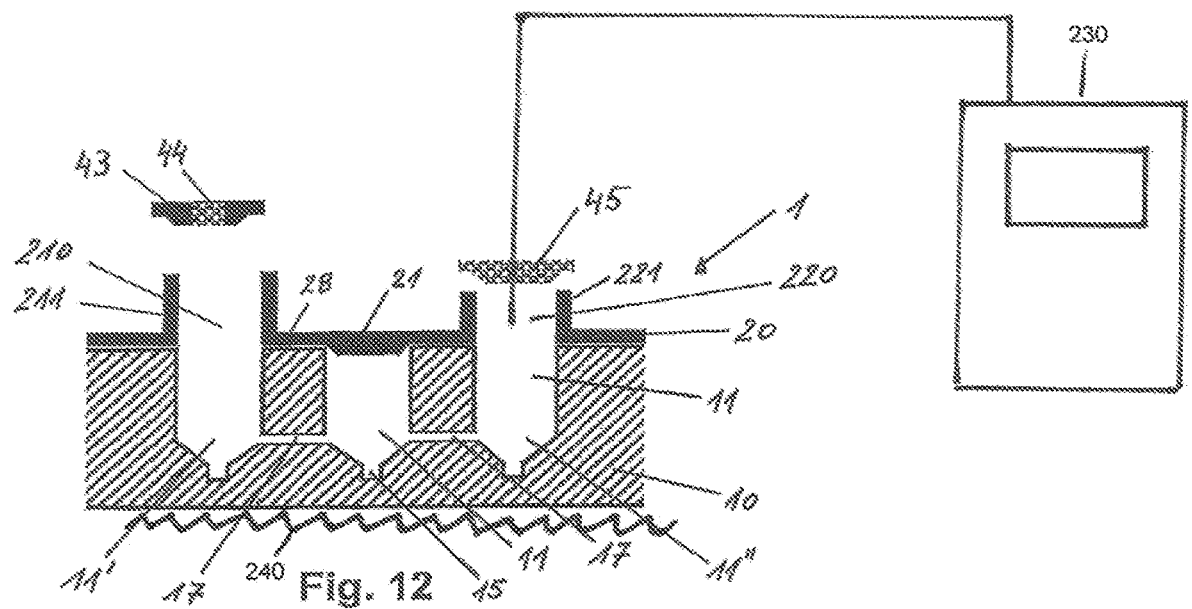
FIG. 12 shows a cross section through a portion of a further embodiment of the system.

FIG. 12 is a schematic representation of another embodiment of the system (1) for propagating microtissues. The multiwell plate (10) is configured such that the neighboring wells (11, 11', 11") of one row of wells of the multiwell plate

(10) are in fluid connection with one another by means of at least one channel (17) connecting the wells.

In addition, the embodiment comprises a plate sealing means (20), comprising an inlet opening (210) and an outlet opening (220). The inlet opening (210) is placed instead of the first bulge of a row of bulges, whereas the outlet opening (220) is placed instead of the last bulge of the row of bulges.

The inlet opening (210) and/or the outlet opening (220) may be configured as through holes in the silicone mat. In an alternative embodiment the inlet opening (210) and/or the outlet opening (220) may be configured as a funnel or chimney which comprises a wall (211, 221) extending substantially upright from the first face (28) of the plate sealing means (20) when mounted to the multiwell plate (10).

The open end of the inlet opening (210) and the open end of the outlet opening may be sealed by means of a plug (43, 45). The plug may be made of a plastic material such as a silicone rubber. In an embodiment, the plug (43) may comprise a microporous section (44). Alternatively, the plug (45) may consist of a microporous material. Sealing the inlet opening and/or the outlet opening of the plate sealing means with a plug consisting of or comprising a microporous material improves the exchange of gaseous fluids in the system (1).

Figure 13:
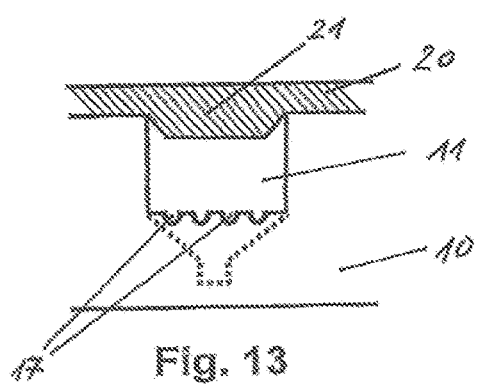
FIG. 13 shows a cross section through a portion of yet another embodiment of the system.

FIG. 13 shows a cross section through a portion of an embodiment of the system comprising a multiwell plate (10) and a plate sealing means (20). The multiwell plate comprises a plurality of wells being in fluid communication with one another. Neighboring wells (11) are put in fluid communication by means of one or more channels (17) extending from one well (11) to the next well in a row of wells.

In a preferred embodiment, the one or more channels connecting neighboring wells is/are not disposed at the lower end of the well, but at a distance in height from the bottom of the wells.

The embodiments shown in FIGS. 12 and 13 allow to supply culture medium through the inlet opening of the plate sealing means mounted to the corresponding multiwell plate without the need of removing the plate sealing means (20) from the multiwell plate (10). The culture medium supplied to the first well, i.e. the well underneath the inlet opening (210) will flow through the channels connecting the wells with one another such that all wells being in fluid communication with each other are supplied with culture medium.

The embodiment further provides the opportunity of providing a constant flow of culture medium through the wells being in fluid communication if a constant supply of culture medium through the inlet opening (210) and a constant removal of culture medium through the outlet opening (220) is provided. The constant flow of culture medium may be obtained by utilizing hydrostatic forces in that the level of culture medium in the funnel of the inlet opening is kept higher than the level of culture medium at the outlet opening. The height difference thus provides a hydrostatic force which forces the culture medium flowing through the channels from one well to the next well towards the last well which is the well underneath the outlet opening. The velocity of medium flow through from one well to the next well can also be determined by the diameter and/or number of channels connecting said wells.

Figure 14:
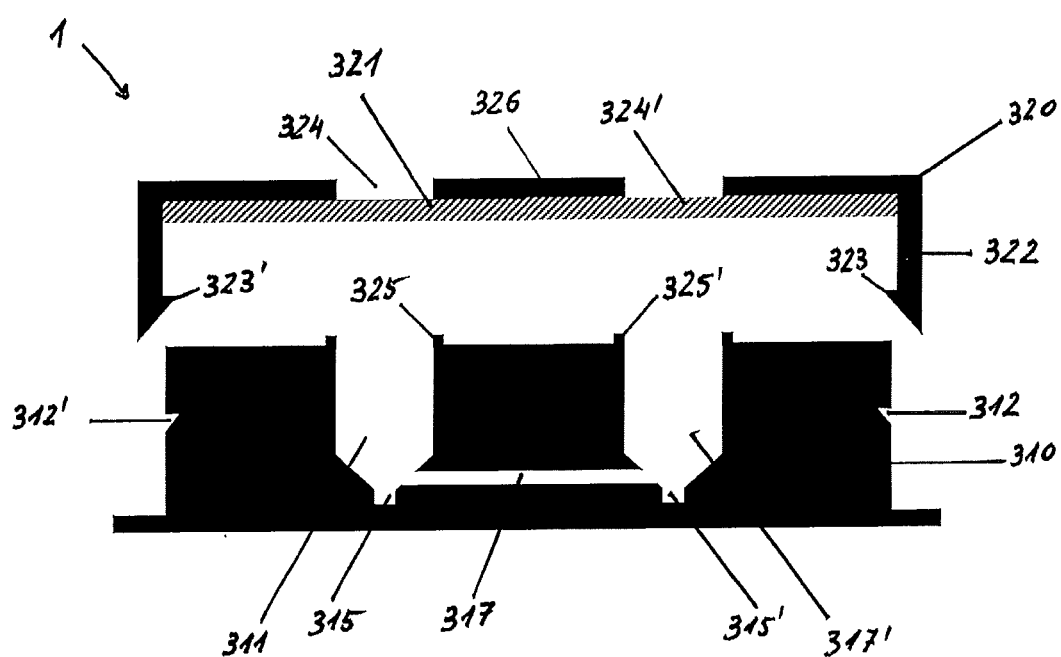
FIG. 14 is a cross sectional view of another embodiment of a system for propagating cells.

Referring to FIG. 14, another embodiment of the system is shown. The system (1) of this embodiment comprises a multiwell plate (310) and a plate sealing means (320). The multiwell plate (310) comprises wells (311, 311') including microtissue compartments (315, 315'). The wells (311, 311') are in fluid communication due to the channel (317) which is provided between said wells (311, 311'). In addition, each of the wells (311, 311') comprises a circumferential edge (325, 325') protruding from the upper face of the multiwell plate (310). The multiwell plate further comprises grooves (312, 312').

The embodiment further comprises a plate sealing means (320) which is configured as a lid comprising a plate (326) and a circumferential brim (322). Said brim (322) comprises latches (323, 323') at opposite sides of the lid for engaging in the grooves (312, 312') upon correct mounting of the plate sealing means (320) to the multiwell plate (310). The plate sealing means (320) further comprises a planar mat (321) made of a resilient elastomer. Said planar mat (321) may be attached to the plate (326). The plate further comprises through bores (324, 324') which align with the wells (315, 315') of the multiwell plate upon being mounted thereto.

In an embodiment of the first aspect, the system further comprises means for controlling the temperature (240) within the wells of the multiwell plate. The means for controlling the temperature are configured to control the temperature such that the temperature within the wells of the multiwell plate is a temperature of between 25° C. and 37° C.

In an alternative and/or additional embodiment, the means for controlling the temperature within the wells of the multiwell plate are configured to control the temperature during shipping of the multiwell plate being sealed with a plate sealing means according to the first aspect.

In another and/or alternative embodiment of the first aspect, the system further comprises a temperature data logger (230). The temperature data logger (230), also called temperature monitor, is a portable measurement instrument that is capable of autonomously recording the temperature over a defined period of time. The digital data being recorded can be retrieved, viewed and evaluated. The temperature data logger (230) is used to monitor the temperature of the cells being propagated in that the ambient temperature of the cell culture is measured. Using the temperature data logger (230) is advantageous when the cells or microtissues are shipped. The temperature data logger (230) is included in the container bearing the cell culture to be shipped within at least one sealed multiwell plate. The temperature data logger (230) is preferably placed in close proximity to the at least one multiwell plate including the cells or microtissues. The temperature data logger 230) monitors the temperature and alterations in temperature within the container and thus the temperature said cells or microtissues are exposed to. This temperature monitoring permits use of only those cells or microtissues for any assay that were not exposed to undesired temperatures or inadequate temperatures.

Figure 15:
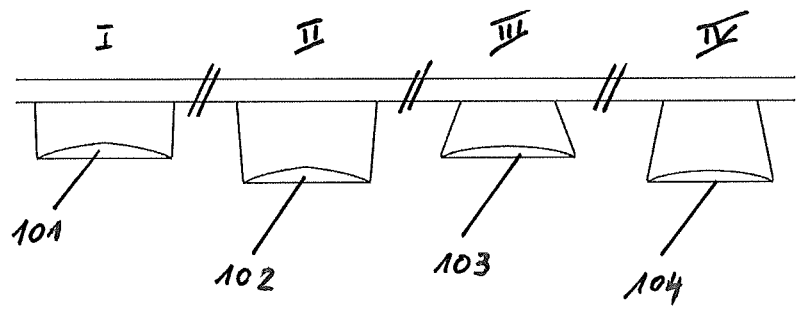
FIG. 15 *a-c* shows various embodiments of bulges of a plate sealing means in cross sectional views.
Figure 15:
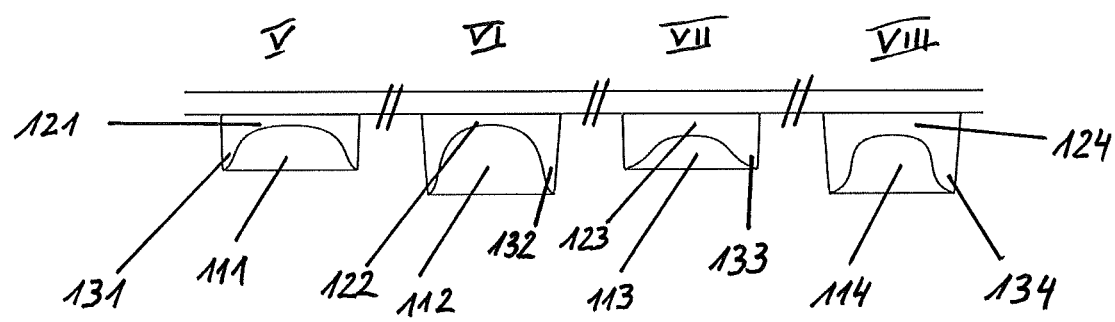
Figure 15:
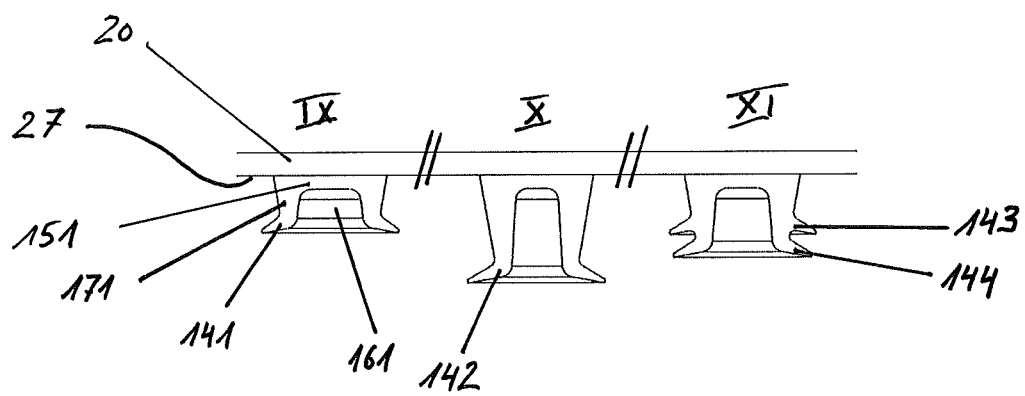

Referring to FIG. 15 a to c various embodiments of bulges are shown schematically in cross-sectional views. FIG. 15 a shows embodiments (I to IV) configures as a frustrum of a cone, wherein the bulges comprise a concave bottom (101, 102, 103, 104). Embodiments III and IV are configured as inverse frustrum of a cone. FIG. 15 b shows embodiments (V to VIII) wherein the bulges comprise a hollow out (111, 112, 113, 114). The bulges comprise a solid portion at their base (121, 122, 123, 124) and a circumferential rim (131, 132, 133, 134) at their distal portion. FIG. 15 c shows embodiments of bulges comprising a single flap (embodiments IX and X) of a double flap (embodiment XI). The single flaps (141, 142) and the double flap consisting of two flaps (143 and 144) are configured at the outer wall of the bulge where they extend outwards and circumferentially from the circumferential rim of the bulge. In the embodiments shown, the flaps (141, 142 and 144) are arranged at the distal end of the bulge. The bulges as shown comprise a solid base, a hollow out and a circumferential rim as exemplified with respect to embodiment IX, wherein the solid base (151) extends perpendicular from the second face (27) of the plate sealing means (20). The bulge comprises a hollow out (161) providing a circumferential rim (171) which further extends from the plate sealing means.

Upon inserting a bulge comprising a concave bottom, a hollow out and/or at least one rim into a corresponding well, the distal portion of said bulge can better snuggle to the inner lining of the wall of the well and thereby provide an even better sealing of the well than a solid bulge.

It is understood that the dimensions of a bulge may vary upon the dimension of the well to be sealed, and that bulges of different heights may be provided.

According to the second aspect, the invention provides a method of propagating cells, wherein cells are provided and propagated in at least one well of a multiwell plate according to the system, said at least one well of the multiwell plate being sealed with a plate sealing means according of the system.

The method comprises the steps of:
providing a multiwell plate as described herein before;
introducing a suspension comprising at least one cell into at least one well of the multiwell plate;
sealing at least the well of the multiwell plate bearing the suspension containing at least one cell with a plate sealing means as described herein before.

In an embodiment of the method, said cells are eukaryotic cells. In a further and/or additional embodiment, the cells are mammalian cells. In yet a further and/or alternative embodiment, the cells are human cells.

In an embodiment of the method, the cells are propagated, propagating the cells at a temperature of between 4° C. and 37° C., preferably at a temperature of between 18° C. and 37° C., more preferably at a temperature of between 25° C. and 37° C., and most preferably at a temperature of between 29° C. and 37° C. for a period of time. Alternatively at a temperature of between 18° C. and 27° C., preferably at a temperature of between 21° C. and 25° C.

The temperature for cultivating and/or shipping cells is preferably maintained constant by utilizing suitable means of controlling the temperature.

In an embodiment of the method, the propagation comprises providing an exchange of culture medium. Said exchange of culture medium may be performed continuously or discontinuously.

In an embodiment, wherein the culture medium is discontinuously exchanged in individual wells of the system, an injection needle is poked through the plate sealing means, preferably through a self-sealing septum of the bulge sealing said well, and inserted into the well. If already present, the culture medium in the well is aspirated through the needle, and fresh culture medium is supplied to the well through the needle.

In an embodiment wherein the culture medium is continuously exchanged in individual wells of the system, an inlet conduit and an outlet conduit are inserted through the plate sealing means, preferably through one or more self-sealing septa of the bulge sealing said well, into the well. A continuous flow of culture medium through the well is then provided by supplying the culture medium through the inlet conduit and by removing culture medium through the outlet conduit.

In an embodiment wherein a system comprising one or more wells being in fluid communication with each other, a continuous exchange of culture medium can be provided in that fresh culture medium is supplied through the inlet opening of the plate sealing means while being mounted to the corresponding multiwell plate, and removing culture medium through the outlet opening of the plate sealing means.

In an additional and/or alternative embodiment, the flow of culture medium is generated by utilizing hydrostatic forces. For example in that the level of culture medium in/above the inlet opening is kept higher than in/above the outlet opening. In an alternative embodiment, a flow of culture medium through the wells being in fluid communication with each other can be achieved in that the system is placed on a rocker and seesawing the system.

According to the third aspect, the invention provides the use of the system as described herein before for propagating cells, preferably eukaryotic cell, more preferably mammalian cells, and particularly preferably human cells, most preferably in form of a microtissue or spheroid.

In an embodiment of the third aspect, the use of the system for propagating cells and/or microtissues comprises the use of the system for shipping cells and/or microtissues. The system for propagating cells and/or microtissues is particularly advantageous for shipping cells and/or microtissues due to the tight sealing of the wells of the multiwell plate by the corresponding plate sealing means and its properties. The use of the system for shipping cells and/or microtissues provides better survival rates and better viability of the cells and/or microtissues at their destination. Particularly advantageous is that the cells and/or microtissues can be shipped at a temperature of between 18° C. and 27° C., preferably at a temperature of between 21° C. and 25° C., and that it is not necessary to ship the cells and/or microtissues in frozen or deep frozen conditions for maintaining their survival and viability at a desirable level.

According to further aspects, the invention provides multiwell plates as described herein above as part of the system according to the first aspect, and plate sealing means as described herein above as part of the system according to the first aspect.

The invention claimed is:

1. A system for propagating cells, said system comprising a multiwell plate and a plate sealing means for sealing at least one well of the multiwell plate,
   wherein at least two wells of the multiwell plate are in fluid connection with one another by means of at least one channel connecting said two wells, and
   wherein the plate sealing means comprises at least one solid bulge or at least one bulge comprising a solid base, said bulge consisting of a resilient elastomer, and being configured to securely fit into the at least one well of the multiwell plate,
   wherein the plate sealing means comprises at least two openings arranged at positions of said at least two wells that are in fluid connection with one another, thereby providing an inlet opening and an outlet opening present in the system, and
   wherein the system further comprises at least two plugs for sealing the inlet opening and outlet opening, respectively.

2. The system according to claim 1, wherein at least a portion of at least one well of the multiwell plate is provided with an ultra-low attachment surface.

3. The system according to claim 1, wherein the at least one bulge comprises a rim configured to be seated on the edge of a well.

4. The system according to claim 1, wherein the at least one bulge comprises at least one re-sealable septum.

5. The system according to claim 1, wherein the inlet opening is provided with a funnel or chimney.

6. The system according to claim 1, wherein the outlet opening is provided with a funnel or chimney.

7. The system according to claim 1, wherein the plate sealing means is present in form of a mat or in form of a lid, said lid comprising a hard plastic frame and a plane portion comprising at least one bore aligning with a well of the multiwell plate upon, said at least one bore being closed with said bulge.

8. The system according to claim 1, wherein the resilient elastomer has an oxygen permeability of more than $1*10^9$, cm3*cm/(s*cm2*cmHg).

9. The system according to claim 1, wherein the resilient elastomer is selected from the group consisting of silicone rubber, nitrile rubber and natural rubber.

10. The system according to claim 9, wherein the silicone rubber is at least one of dimethylsilicone rubber vinyl methyl siloxane and phenyl vinyl methyl siloxane.

11. The system according to claim 1, further comprising a controller for controlling the temperature within the wells.

12. The system according to claim 1, further comprising a temperature data logger as a portable measurement instrument.

13. The system of claim 1, wherein the inlet opening corresponds to a first well of a row of wells in fluid connection with at least a second row of wells and the outlet opening corresponds to the last well of a row of wells in fluid connection with a first row of wells.

14. A process for propagating cells, the process comprising the steps of:
providing a system according to claim 1;
introducing a suspension comprising at least one cell into at least one well of said at least two wells of the multiwell plate that are connected with one another;
sealing the multiwell plate bearing the suspension containing at least one cell with the plate sealing means.

15. The process according to claim 14, further comprising propagating the cells at a temperature of between 4° C. and 37° C.

16. The process according to claim 14, further comprising continuously or discontinuously replacing culture medium.

17. A process of propagating cells comprising providing and propagating said cells in at least one well of a multiwell plate of a system according to claim 1.

18. A pharmacological test assay comprising cultivating cells in a system according to claim 1 and testing the toxicity of a drug or a chemical compound on said cells.

19. The pharmacological test assay according to claim 18, wherein the multiwell plate comprises at least two wells being in fluid communication, a first well and a second well, the first well containing a first microtissue and the second well containing a second microtissue, wherein the pharmacological test assay comprises providing a chemical compound to the first microtissue, and allowing a reaction of said second microtissue and analyzing the same.

* * * * *